US008562622B2

(12) United States Patent
Daniel (10) Patent No.: US 8,562,622 B2
(45) Date of Patent: Oct. 22, 2013

(54) SUTURING DEVICE WITH SUTURING CAPSULE REMOVAL MECHANISM

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 13/626,935

(22) Filed: Sep. 26, 2012

(65) Prior Publication Data

US 2013/0079801 A1 Mar. 28, 2013

Related U.S. Application Data

(60) Provisional application No. 61/539,485, filed on Sep. 27, 2011.

(51) Int. Cl.
*A61B 17/04* (2006.01)
*A61B 17/12* (2006.01)

(52) U.S. Cl.
USPC .......................................................... 606/114

(58) Field of Classification Search
USPC ........................................ 606/139, 144–148
See application file for complete search history.

(56) References Cited

U.S. PATENT DOCUMENTS 8,123,764 B2 * 2/2012 Meade et al. ................. 606/145
2011/0118758 A1 5/2011 Sauer

FOREIGN PATENT DOCUMENTS

WO 2006034209 A2 3/2006
WO 2011009464 A2 1/2011

* cited by examiner

*Primary Examiner* — Gary Jackson
*Assistant Examiner* — Lindsey Bachman
(74) *Attorney, Agent, or Firm* — Coloplast Corp., Coloplast A/S; Nick Baumann (57) ABSTRACT

A suturing assembly includes a handle and a head located distal to the handle. The handle includes an actuator coupled to a distal half of the handle. The head defines a head perimeter and includes a needle port and a capsule cavity located within the head perimeter. The needle port stores a needle that is connected with the actuator by a rod and the capsule cavity is sized to retain a suture capsule attached to a length of suture. A release mechanism is attached to the rod and located on the distal half of the handle. The needle is movable within the head perimeter to engage with the suture capsule and place the suture capsule into the needle port, and the release mechanism is operable to move the rod a distance in a proximal direction to separate the suture capsule from the needle.

9 Claims, 13 Drawing Sheets

SUTURING DEVICE WITH SUTURING CAPSULE REMOVAL MECHANISM

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon digitally palpates a desired location for placement of the suture and is unable to see the suture site.

Improved suturing instruments and improved methods of delivering sutures would be welcomed by the surgical staff.

SUMMARY

One aspect provides a tissue suturing device including a handle and a head located distal to the handle. The handle includes an actuator coupled to a distal half of the handle. The head defines a head perimeter and includes a needle port and a capsule cavity located within the head perimeter. The needle port stores a needle that is connected with the actuator by a rod and the capsule cavity is sized to retain a suture capsule attached to a length of suture. A release mechanism is attached to the rod and located on the distal half of the handle. The needle is movable within the head perimeter to engage with the suture capsule and place the suture capsule into the needle port, and the release mechanism is operable to move the rod a distance in a proximal direction to separate the suture capsule from the needle.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

In this specification, shunt means to move an object away from a first axis to another axis that is different from the first axis. For example, in one embodiment a suturing device includes a needle that is moved in a first direction (e.g., along a longitudinal axis) and is subsequently moved in a second direction different from the first direction (i.e., away from the longitudinal axis); thus the needle is shunted away from a longitudinal axis when deployed from the device.

In this specification, proximal is that location that is nearest a user of the suturing assembly described below.

In this specification, end means endmost and end portion means that segment that is adjacent to and extends from the end. For example, a proximal end is that end location of a handheld instrument that is nearest a user, and a proximal end portion is that segment (e.g., a handle of the handheld instrument) that is adjacent to and extends distally away from the proximal end.

Embodiments provide a suturing device for intracorporeal suturing that throws a suture through tissue and allows a suture capsule attached to the suture to be removed from the device with the use of one hand only. The suturing device is operable to place sutures to treat pelvic organ prolapse. The placement of such sutures sometimes requires one hand to serve as a guide to direct a location of the suturing needle while the second hand operates an actuator that moves the suturing needle through the tissue. Embodiments provide the suturing device with a mechanism that allows the same hand that is used to operate the actuator to also disengage the suture from the suturing needle.

Figure 1:
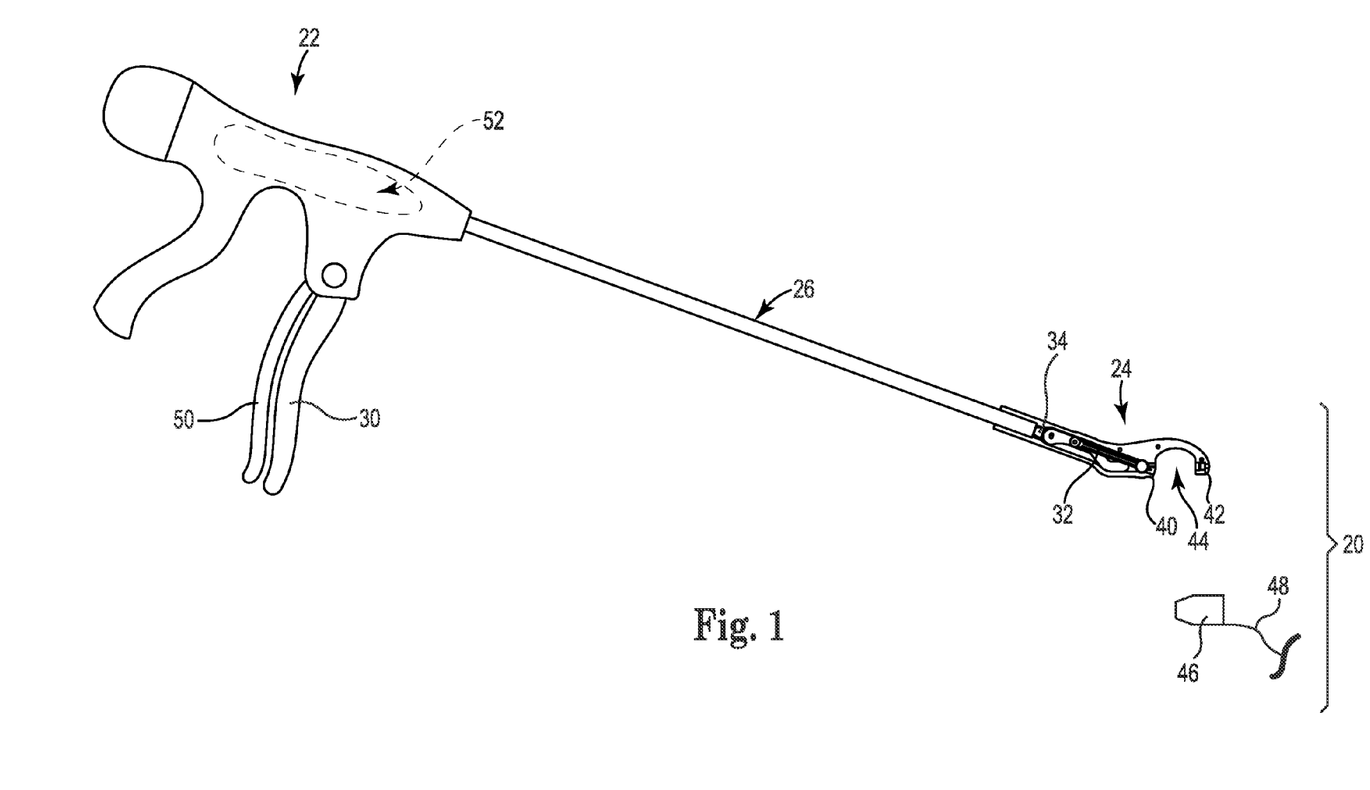
FIG. 1 is a side view of one embodiment of a tissue suturing device.

FIG. 1 is a side view of one embodiment of a tissue suturing device 20. The tissue suturing device 20 (device 20) includes a handle 22 and a head 24 that is connected to the handle 22 by a shaft 26. The handle 22 includes an actuator 30 that is connected to a needle 32 by a rod 34 that extends through the shaft 26. The head 24 provides a needle port 40 through which the needle 32 moves in/out and a capsule cavity 42 that is separated from the needle port 40 by a throat 44. The capsule cavity 42 is sized to retain a suture capsule 46 that is attached to a length of suture 48. The actuator 30 is operable to move the needle 32 out of the needle port 40 to engage with the suture capsule 46 and retrieve the suture capsule 46 back to the needle port 40 to facilitate suturing tissue.

In one example of the use of the device 20, the surgeon will hold the handle 22 in one hand (for example the right hand) and guide the head 24 to an intracorporeal location within the patient with the other hand (e.g., the left hand). The device 20 is useful for placing a suture in the sacrospinous ligament inside the pelvis through what some call a blind approach in which the head 24 enters the pelvis through a vaginal incision. The actuator 30 is manipulated by the fingers of the right hand to move the needle 32 across the throat 44 to penetrate tissue before engaging with the suture capsule 46. The needle 32 pulls the suture capsule 46 and the suture 48 across the throat 44 to "throw" a suture through the ligament or tissue. The suture capsule 46 is parked into the needle port 40, which allows the surgeon to retract the shaft 26 and the head 24 from the pelvis of the patient and prepare the device 20 for placement of another suture.

It is desirable for the surgeon to physically contact and identify the target location in the pelvis with the left hand so that the head 24 may be directed back to the target location in a blind approach. The device 20 provides a release lever 50 that is connected with a release mechanism 52 that allows the surgeon to disengage the suture capsule 46 from the needle port 40 with the same hand (right hand) that activated the actuator 30. The release mechanism 52 allows the surgeon to use one hand (the left hand) to mark the target location and the right hand to both throw the suture 48 and separate the suture capsule 46 from the needle port 40. In particular, the release mechanism 52 is operable to move the rod 34 an added small distance in a proximal direction to separate the suture capsule 46 from the needle 32.

It is to be understood that the device 20 is suited for left-hand use allowing the right hand to mark the target location.

The tissue suturing device 20 is suited for the intracorporeal suturing of tissue during surgery, and in one embodiment is provided as a sterile, disposable surgical instrument that is suited to be discarded after the surgical procedure. To this end, the components of device 20 are selected to be compatible with gas, steam, or radiation sterilization.

Figure 2A:
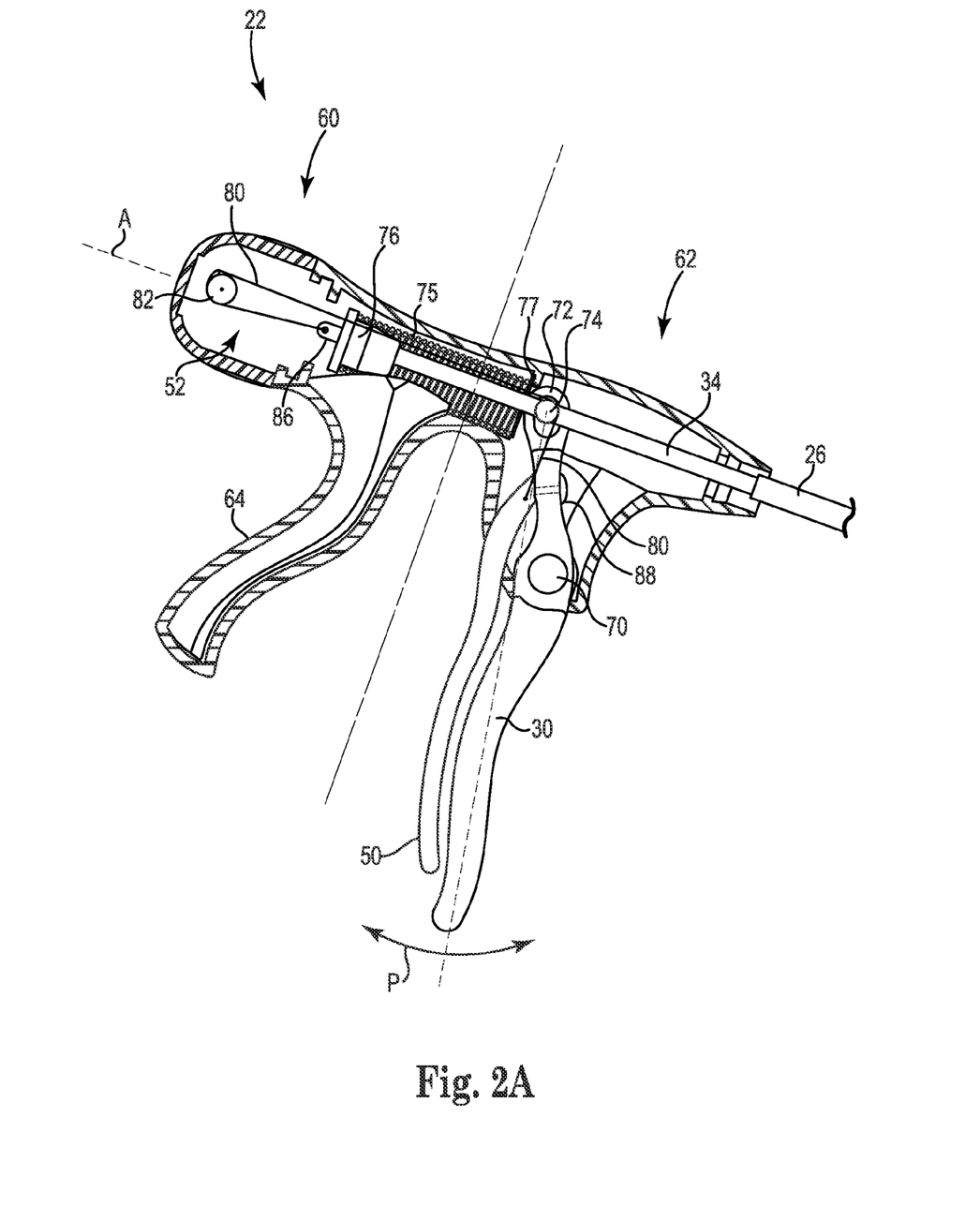
FIG. 2A is a cross-sectional view of one embodiment of a handle of the tissue suturing device illustrating an actuator and a release mechanism.

FIG. 2A is a side cross-sectional view of the handle 22. The handle 22 is generally fabricated from plastic and in one acceptable configuration is formed as a pair of mating clamshell halves that fit together to retain the actuator 30, the rod 34, and the release mechanism 52. The view of FIG. 2A shows one half of the mating clamshell structured removed.

The handle 22 includes a proximal half 60 and a distal half 62. A thumb brace 64 is provided on the proximal half 60 and the actuator 30 and a release lever 50 are attached to the distal half 62 of the handle 22. In one embodiment, both of the actuator 30 and the release lever 50 extend through a bottom surface of the handle 22.

In one embodiment, the actuator 30 is operably engaged with the rod 34 by attaching the actuator 30 at a pivot point 70 to the handle 22 and attaching a slotted head 72 to a pinion 74 of the rod 34. A spring 75 is provided to bias the rod 34, and the spring 75 is captured between a spring pusher 76 and a rib 77 maintained inside of the handle 22. With reference to FIG. 1, the actuator 30 pivots about the pivot point 70 to move the rod 34 in a distal direction, which moves the needle 32 in a distal direction out of the needle port 40. The spring 75 biases the rod 34 to move the rod 34 in the proximal direction to retrieve the suture capsule 46 and park it in the needle port 40. The release mechanism 52 is provided to move the rod 34 an additional distance in the proximal direction (e.g., rearward) to separate the suture capsule 46 from the needle 32.

In one embodiment, the release mechanism 52 includes a cable 80, a pulley 82, and the release lever 50. The cable 80 is connected to a proximal end 86 of the rod 34 and extends over both the pulley 82 and the pinion 74 and is connected to the release lever 50. In one embodiment, the release lever 50 is connected to the actuator 30 by a pin 88.

The actuator 30 is connected with the rod 34 and is configured to move in a plane P that is parallel with a longitudinal axis A of the rod 34. That is to say, the actuator 30 moves "in the plane of the paper" relative to the drawing of FIG. 2A. The release lever 50 is connected to the actuator 30 by the pin 88 and is configured to move with the actuator 30 in the plane that is parallel with the longitudinal axis A of the rod 34. In one embodiment, the release lever 50 is additionally configured to move substantially perpendicular with the plane P that is parallel with the longitudinal axis A of the rod 34, which is in a direction "into the paper" relative to the drawing of FIG. 2A. The release lever 50 thus has two degrees of freedom: in the plane P and not in the plane P. Specifically, as the surgeon holds the handle 22 with a thumb braced against the thumb brace 64, the fingers move the actuator 30 back-and-forth along the longitudinal direction of the rod 34 to throw the suture and the release lever 50 is movable in a lateral direction left and right to disengage the suture capsule 48 from the needle 32.

Figure 2B:
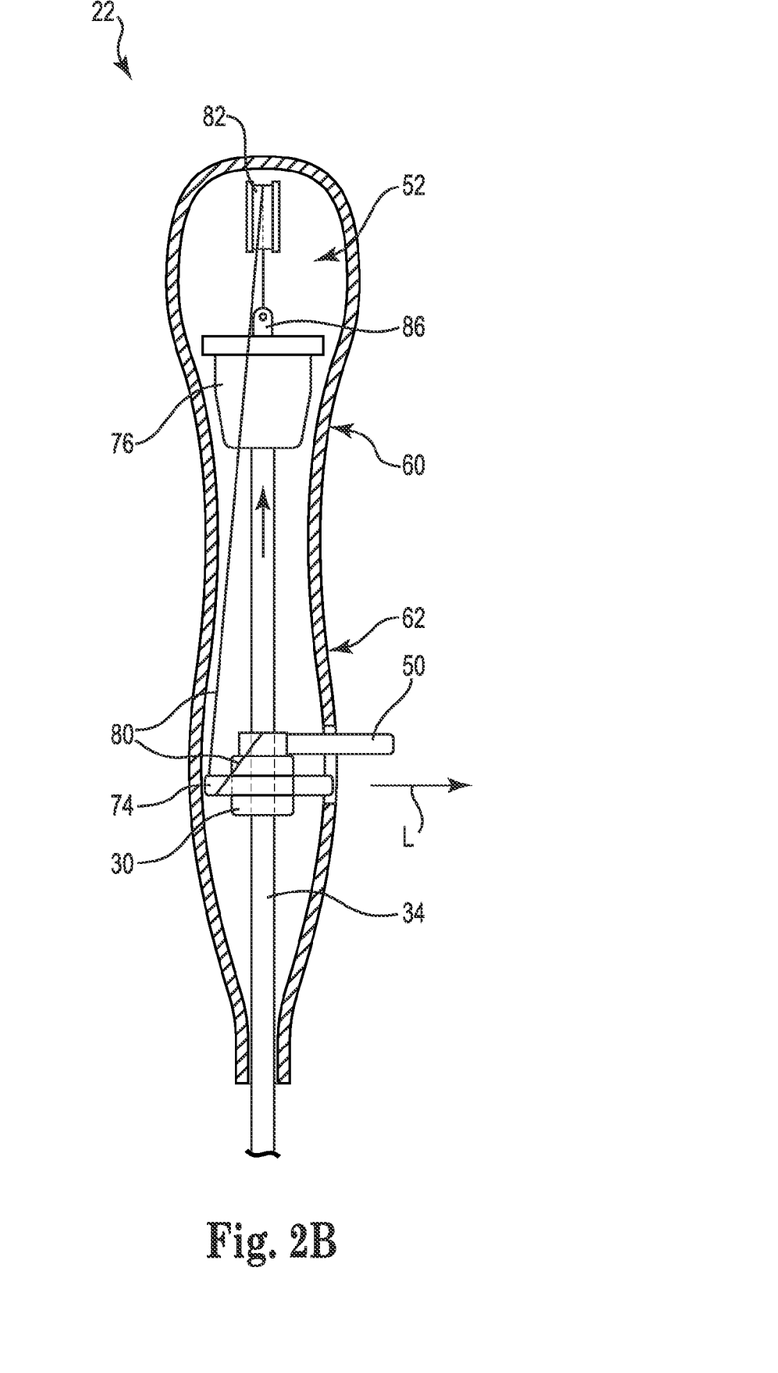
FIG. 2B is a top view of the handle and the release mechanism illustrated in FIG. 2A.

FIG. 2B is a top cross-sectional view of the handle 22. The spring pusher 76 is illustrated inside of the handle 22 but the spring 75 and the rib 77 (FIG. 2A) are removed from the drawing for ease of illustration of the release mechanism 52.

The actuator 30 is coupled to the rod 34 by the pinion 70. The release lever 50 is illustrated in a release position after having been moved a distance in the lateral direction L.

The release mechanism 52 is configured to move the rod 34 a distance in the proximal direction toward the proximal half 60 of the handle 22 when the release lever 50 is moved laterally. The cable 80 is connected between a release lever 50 and a proximal end 86 of the rod 34. Specifically, a portion of the cable 80 that extends from the proximal end 86 is engaged with the pulley 82 and extends in a distal direction within the handle and is engaged around the pinion 74. The movement of the release lever 50 in the lateral direction L creates tension and the cable 80 that is transferred across the pulley 82 to draw the proximal end 86 of the rod 34 an additional distance in the proximal direction. In one embodiment, the release mechanism 52 is operable to move the rod 34 by a distance of between about 0.5-2 mm in the proximal direction, which is sufficient to separate the suture capsule 48 from the needle 32 (FIG. 1).

Figure 3:
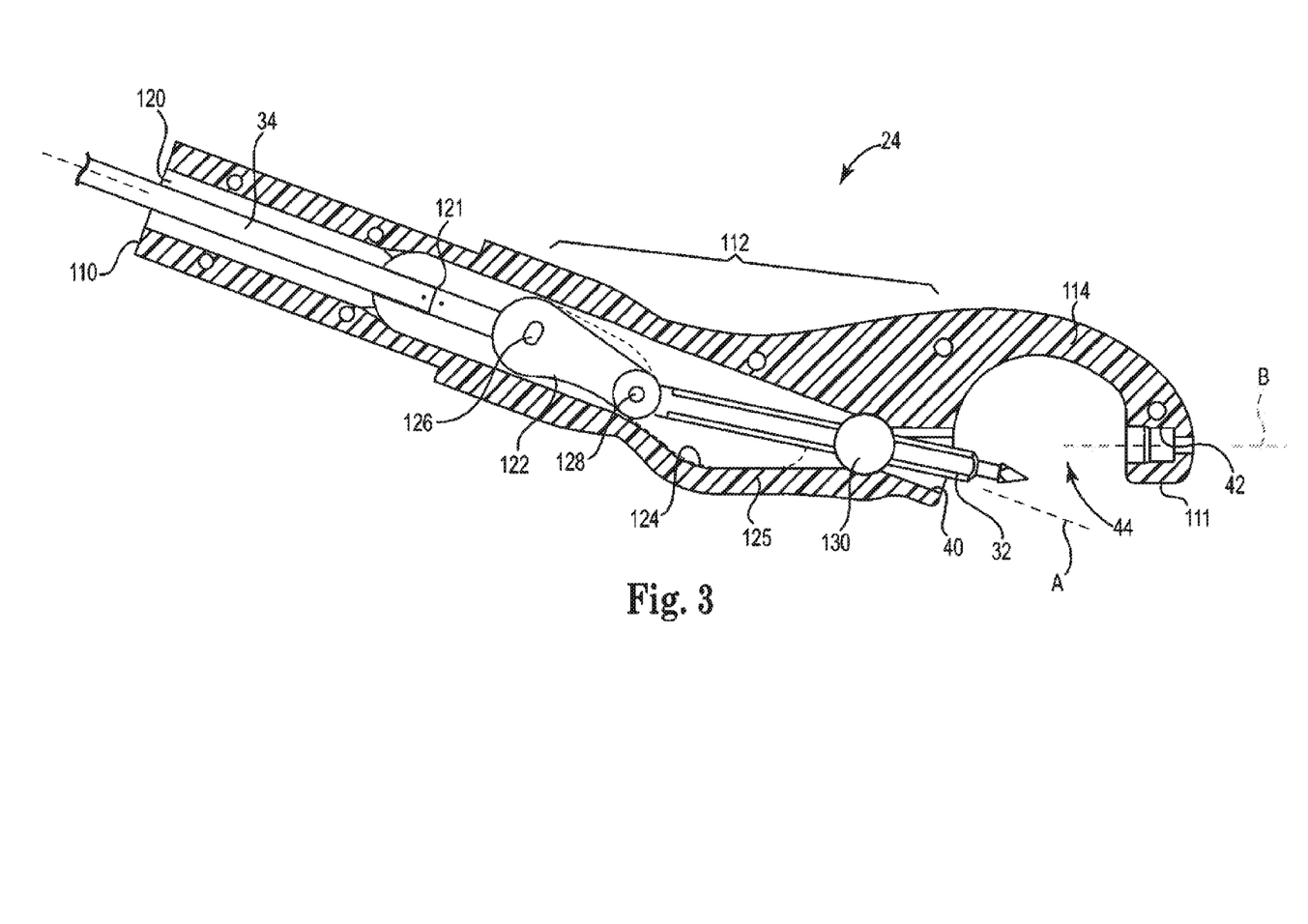
FIG. 3 is a cross-sectional view of one embodiment of a head of the tissue suturing device illustrated in FIG. 1.

FIG. 3 is a side cross-sectional view of the head 24 showing the needle 32 protruding out of the needle port 40. The capsule cavity 42 is empty. It is to be understood that the needle 32 is typically parked in the needle port 40 when the actuator 30 is in a neutral position and the suture capsule 48 is retained within the capsule cavity 42, which "loads" the device in a state ready for use. In one acceptable configuration the head 24 is molded from plastic, for example from a polyetherimide plastic sold under the trademark Ultem, or from glass-filled polyetherimide plastics also sold under the trademark Ultem.

In one embodiment, the head 24 includes a proximal end 110 opposite a distal end 111, a proximal end portion 112 extending from proximal end 110, and a neck 114 that extends from the proximal end portion 112 to the distal end 111. The head 24 is attachable to the shaft 26 through an opening 120 such that the rod 34 extends into the proximal end portion 112 and couples with a link 122 that is attached to the needle 32. In one embodiment, the distal end 111 is aligned with an axis B that is offset radially from the longitudinal axis A. Offsetting the distal end 111 from the longitudinal axis A more comfortably positions the shaft 26 for manipulation by the surgeon as the head 24 is engaged with tissue of the pelvic cavity. The shaft 26 may be flexible for manipulation by the surgeon or rigid to allow the surgeon to bear down upon the device 20 during surgery.

In one embodiment, a clevis pin 121 connects a proximal end of the link 122 to the rod 34 and a distal end of the link 122 is coupled to the needle 32. Movement of the rod 34 by the actuator 30 moves the link 122, which moves the needle 32 into and out of the needle port 40 formed in the proximal end portion 112. In one embodiment, a trace 124 is formed on an interior surface 125 of the proximal end portion 112 of the head 24, and the link 122 is configured to translate and rotate within the trace 124 to translate the needle 32 along the axis A and pitch (or shunt) the needle 32 up/down relative to the axis A. For example, in one embodiment the link 122 includes a first pin 126 that couples with the clevis 121 and a second pin 128 that couples with the needle 32. Axial movement of the rod 34 by the actuator 30 translates to axial movement of the link 122 and the needle 32, and the link 122 rotates about the pins 126, 128 to shunt a path of the needle 32 off of the axis A.

The link 122 is thus configured to translate within the trace 124 to move the needle 32 in/out relative to the needle port 40, and rotate relative to the pins 126, 128 to direct movement of the needle 32 up/down relative to the longitudinal axis A. In one embodiment, the proximal end portion 112 includes a guide pin 130 that defines a bore sized to receive the needle 32. The needle 32 is configured to slide through the bore formed in the guide pin 130, and the guide pin 130 is rotatable to allow the needle 32 to pitch relative to the longitudinal axis A as the needle 32 moves axially, for example as the needle 32 moves into engagement with the distal end 111. In one embodiment, the release mechanism 52 (FIG. 2B) is configured to move the rod 34 an additional distance in the proximal direction to shear the suture capsule 46 against the guide pin 130.

The neck 114 extends between the proximal end portion 112 and the distal end 111 and defines the throat 44. The needle 32 is movable from the proximal end portion 112, out of the needle port 40, across the throat 44, and into the capsule cavity 42 formed in distal end 111. In one embodiment, the distal end 111 and the capsule cavity 42 are both radially spaced away from the longitudinal axis A, and the guide pin 130 rotates to enable the needle 32 to move out of the needle port 40, pitch upwards, and into the capsule cavity 42. In one embodiment, a top surface of the neck 114 defines an open, exposed groove (not shown) that is configured to receive and guide the suture 48 that is attached to the capsule 46 (FIG. 1).

Figure 4:
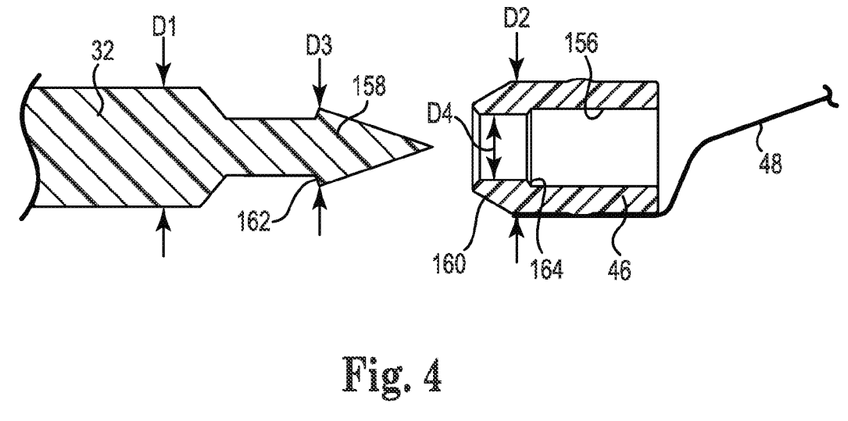
FIG. 4 is a cross-sectional view of a suture and a capsule employed by the tissue suturing device illustrated in FIG. 1.

FIG. 4 is a side view of the needle 32 aligned for engagement with the capsule 46 that is attached to the suture 48. The needle 32 is preferably machined from metal such as stainless steel or a shape memory alloy such as NiTiNOL (Nickel Titanium Naval Ordinance Laboratory), as examples. In one embodiment, the capsule 46 is molded from plastic and formed integrally around an end of the suture 48. Suitable plastic materials for fabricating capsule 46 include polypropylene, polysulfone, urethane, or polyetherimide as examples. Suture 48 includes monofilament suture, braided suture, coated suture materials, absorbable suture, bioabsorbable suture or the like, as examples.

In one embodiment, the needle 32 is shaped to promote secure engagement with the capsule 46 and a leading end 158 is formed to have a conical point with a shoulder 162 that is sized to be pressed into engagement with a flange 164 of a recess 156. For example, the flange 164 is shaped and sized to frictionally engage (e.g., snap-fit) in a "locked" manner with a shoulder 162 of the needle 32 as the needle 32 is driven into the recess 156. The capsule 46 is detachable from the needle 32 when the capsule 46 is sheared against the guide pin 130 (FIG. 3).

The conical point of the needle 32 is configured to form a channel when advanced through tissue, and the capsule 46 is sized to be pulled through the channel in the tissue made by the needle 32. In one embodiment, the leading end 160 of the capsule 46 is chamfered and the needle 32 is configured to draw the chamfered (or truncated) end 160 of the capsule 46 first through the tissue. In one embodiment, the leading end 160 of the capsule 46 is a blunt end similar to that illustrated for the trailing end of the capsule 46, and the needle 32 is configured to draw the blunt end of capsule 46 blunt end-first through the tissue.

In one embodiment, the needle 32 has a first diameter D1 and the capsule 46 has a diameter D2, where the diameter D1 is equal to or greater than the diameter D2. In this manner, the capsule 46 is sized to follow the needle 32 and be retracted through the channel formed in the tissue by the needle 32.

The leading end 158 of the needle 32 is sized to frictionally engage with the recess 156 formed in the capsule 46. For example, in one embodiment the leading end 158 has a diameter D3 that is slightly greater than a diameter D4 formed in an opening of the recess 156. In this manner, when the leading end 158 of the needle 32 is inserted into the recess 156, the leading end 158 is forced into and seats within and captures the capsule 46.

FIGS. 5A-5D are side schematic views of the device 20 employed to place the suture 48 through tissue.

Figure 5A:
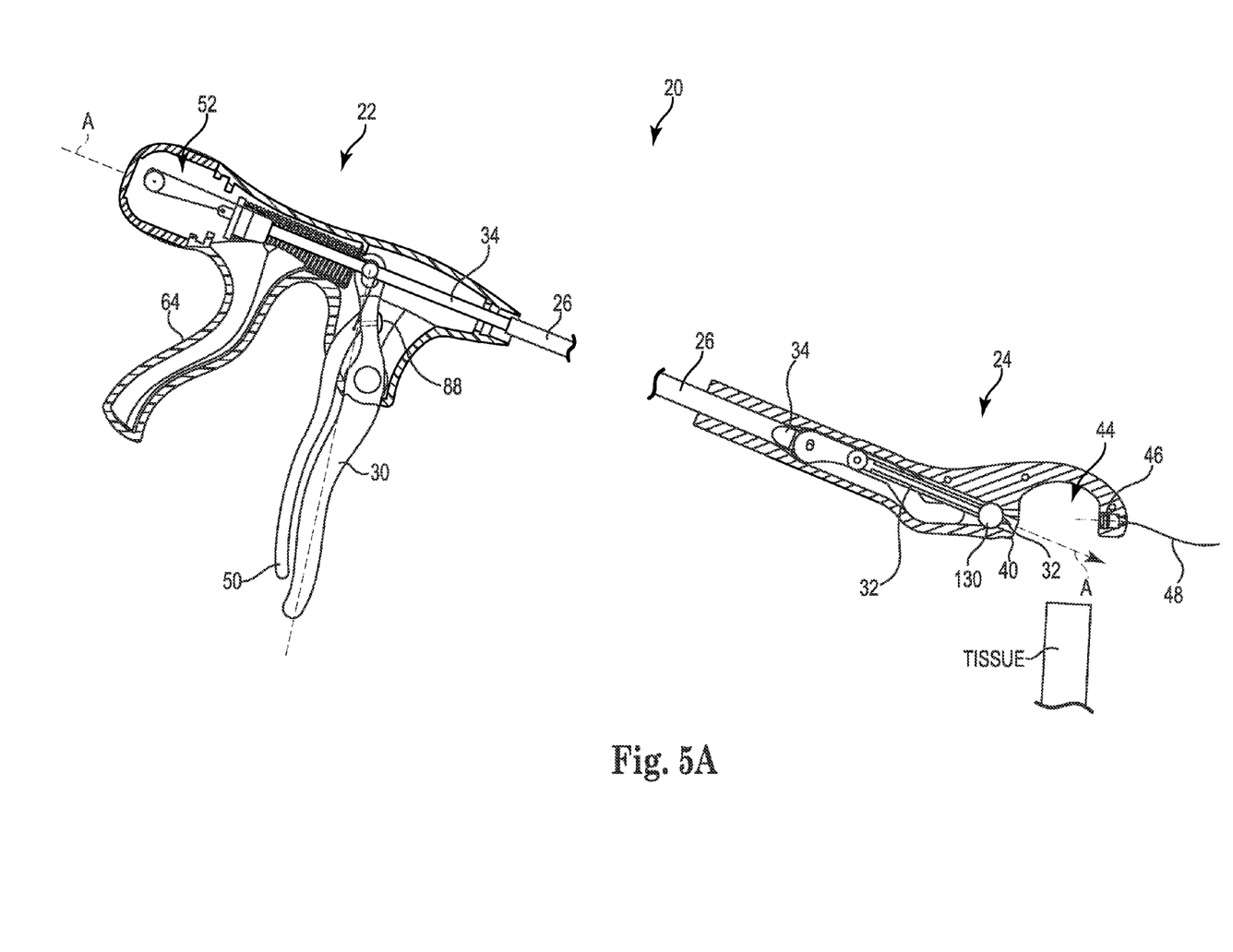
FIGS. 5A-5D are side cross-sectional views of the tissue suturing device illustrated in FIG. 1 employed to place a suture through tissue.

FIG. 5A is a side schematic view of the throat 44 of the head 24 positioned for engagement with tissue. Typically, the head 24 is introduced into the pelvic cavity through an incision made in the vagina and a stitch of the suture 48 is placed in the tissue of the pelvis. For example, the device 20 is suited for placing suture by a blind approach into tissue within the pelvis, such as ligaments like the sacrospinous ligament or a muscle or other tissue.

The actuator 30 and the release lever 50 are in a neutral position and the needle 32 is retracted within the needle port 40. The suture capsule 46 is retained within the cavity 42 and is so positioned for eventual engagement with the needle 32. The suture 48 is illustrated as trailing from the head, but embodiments provide for retaining at least some of the suture 48 on or adjacent to the handle 22.

Figure 5B:
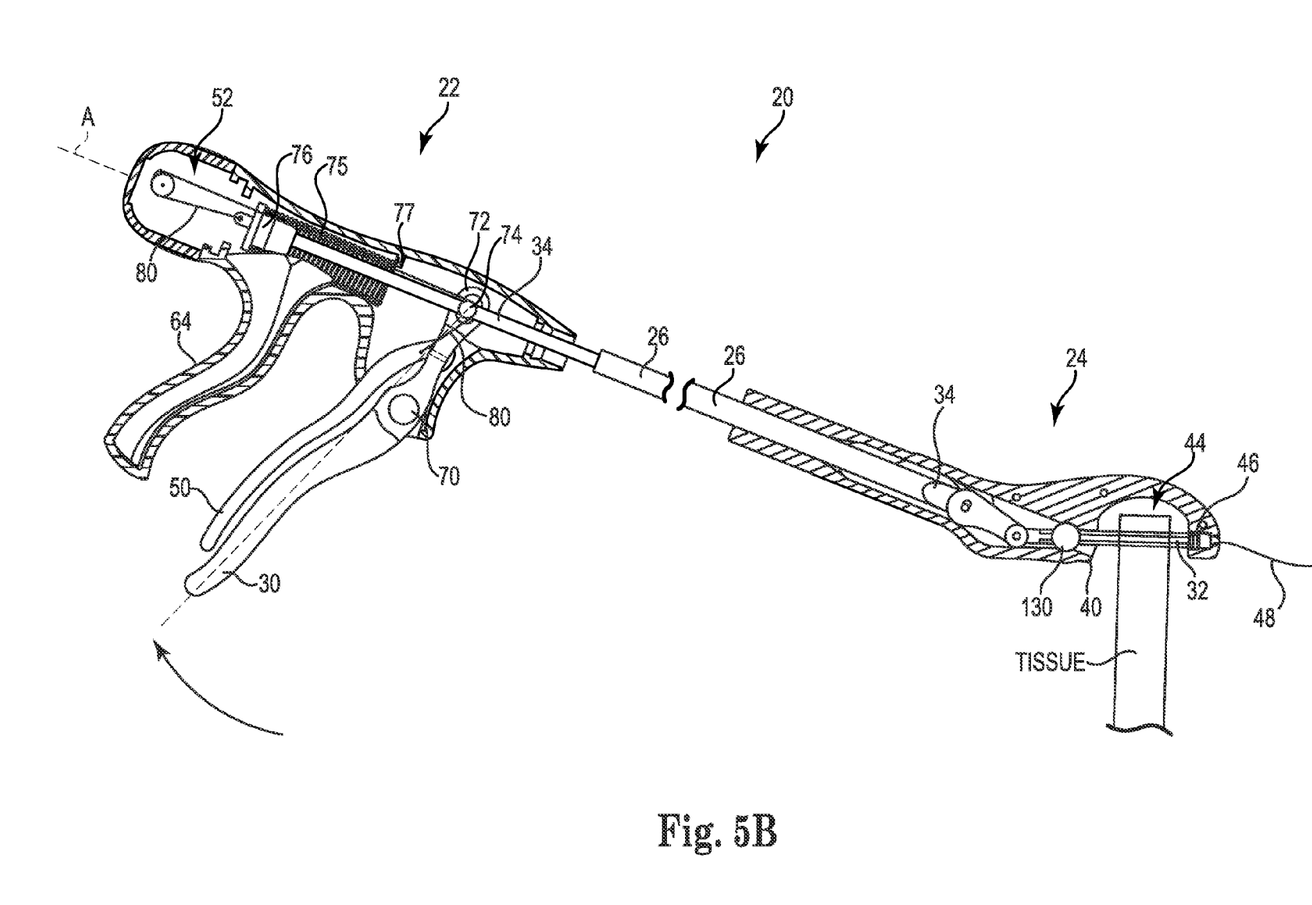

FIG. 5B is a side schematic view of the device 20 activated to drive the needle 32 through the tissue. The actuator 30 and the release lever 50 have been moved in the plane P that is parallel with the longitudinal axis A of the rod 34 in the proximal direction toward the thumb brace 64. The rearward movement of the actuator 30 pivots the actuator 30 on the pivot point 70 and moves the slotted head 72 in the distal direction. The slotted head 72 is engaged with the pinion 74, and movement of the slotted head 72 in the distal direction moves the rod 34 in the distal direction to drive the needle 32 through the tissue. The spring 75 is compressed. The needle 32 moves from the needle port 40 across the throat 44 and is engaged with the suture capsule 46.

The release lever 50 is connected with the actuator 30 by the pin 88. The release lever 50 moves a small distance in the proximal direction when the actuator 34 is squeezed toward the thumb brace 64, which allows the cable 80 to move with the rod 34 as the rod 34 moves in the distal direction.

Figure 5C:
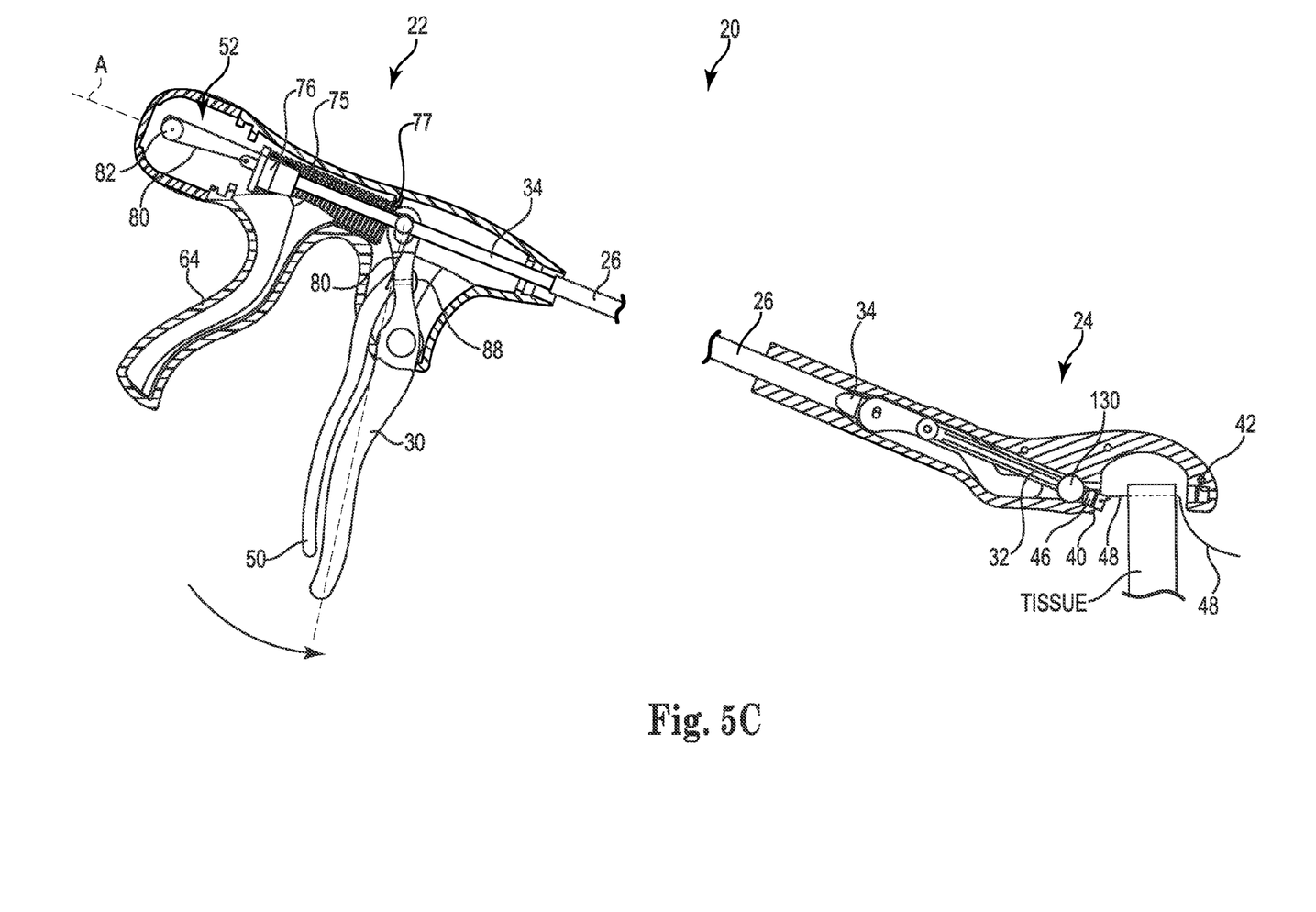

FIG. 5C is a side schematic view of the device 20 with the needle retracted in the proximal direction to draw the suture capsule 46 and the suture 48 through the tissue.

The spring 75 has moved the actuator 30 and the release lever 50 back to the neutral position. In particular, the spring 75 has biased the spring pusher 76 in the proximal direction to pull the rod 34 and the needle 32 rearward (in the proximal direction). The release lever 50 is connected to the actuator 30 by the pin 88 and thus has moves with the actuator 30 in the distal direction to the neutral position that is illustrated in FIG. 5C. The cable 80 of the release mechanism 52 is configured to move as the rod 34 traverses through the tissue.

When the suture 48 is "thrown," the suture capsule 46 is parked within the needle port 40 and the suture 48 disengages from the capsule cavity 42 as it extends through the tissue. The head 24 is thus in condition for removal from the pelvis to allow the surgeon to load another suture capsule 46 into the capsule cavity 42.

Figure 5D:
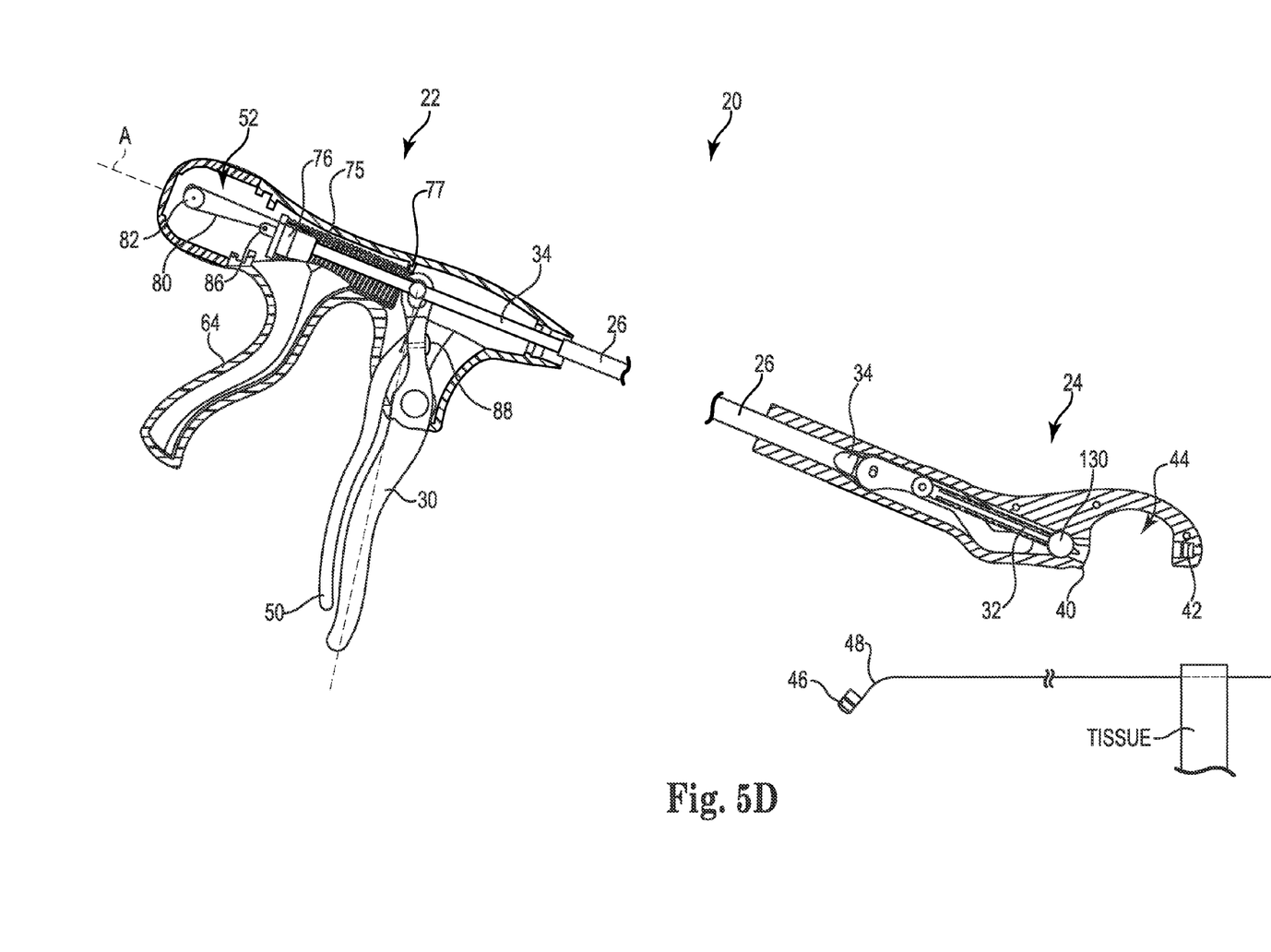

FIG. 5D is a side schematic view of the device 20 with the release mechanism 52 activated to disengage the suture capsule 46 from the needle 32. The release mechanism 52 is typically deployed after removing the head 24 from the target suture site.

The release lever 50 is connected to the actuator 30 by the pin 88, and lateral movement of the release lever 50 (into the paper of the drawing of FIG. 5D) pulls on the cable 80 to draw the rod 34 an additional distance in the proximal direction. In particular, pivoting the release lever 50 about the pin 88 pulls the cable 80 over the pulley 82 to draw the proximal end 86 of the rod 34 backwards, which draws the needle 32 backwards to shear the suture capsule 46 against the guide pin 130. The suture capsule 46 is thus freed from the needle 32 and the head 24 and is typically outside of the pelvis and outside of the patient's body, which provides improved access to the suture 48 and the suture capsule 46.

The suture 48 extends back into the patient's body to the target tissue. The suture 48 may be adjusted by pulling on the suture capsule 46 to draw the suture 48 through the tissue. The surgeon eventually ties the suture 48 and snips the suture capsule 46 off of the suture 48. In one embodiment, the suture 48 is tied to a support material and the length of the suture is employed to draw the support material into the patient's body for fixation to the target tissue.

Figure 6:
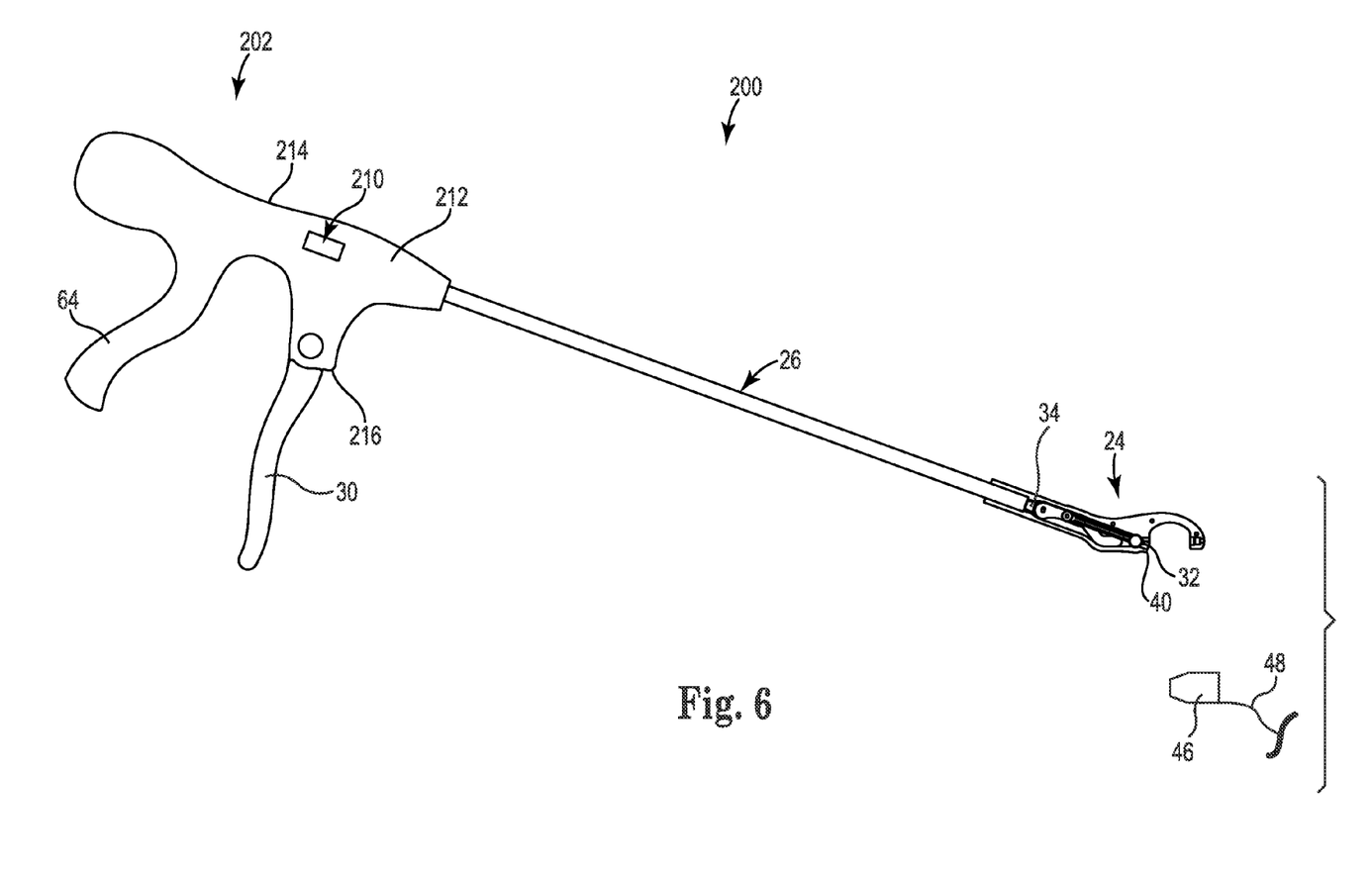
FIG. 6 is a side view and FIGS. 7A-7B are a top cross-sectional views of one embodiment of a tissue suturing device.

FIG. 6 is a side view of one embodiment of a tissue suturing device 200. The tissue suturing device 200 (device 200) includes the head 24, the actuator 30, the needle 32, and the rod 34 retaining their functions as described above and a handle 202 attached to the shaft 26 and the rod 34.

The actuator 30 operates to move the rod 34 and the needle 32 in the distal direction to engage with the suture capsule 46 and in the proximal direction to park the suture capsule 46 in the needle port 40, substantially as described above. In one embodiment, the handle 202 includes a release lever 210 mounted to a side of the handle 202 that operates to separate the suture capsule 46 from the needle 32. The handle 202 includes a side surface 212 extending between a top surface 214 and a bottom surface 216 of the handle 202 and the release lever 210 is conveniently placed to extend through the side surface 216. The actuator 30 extends from the bottom surface 216 similar to the device 20 described above in FIG. 1. The release lever 210 is connected with the rod 34 and extends through the side surface 212 of handle for access by the same hand/fingers of the surgeon that operates the actuator 30.

Figure 7A:
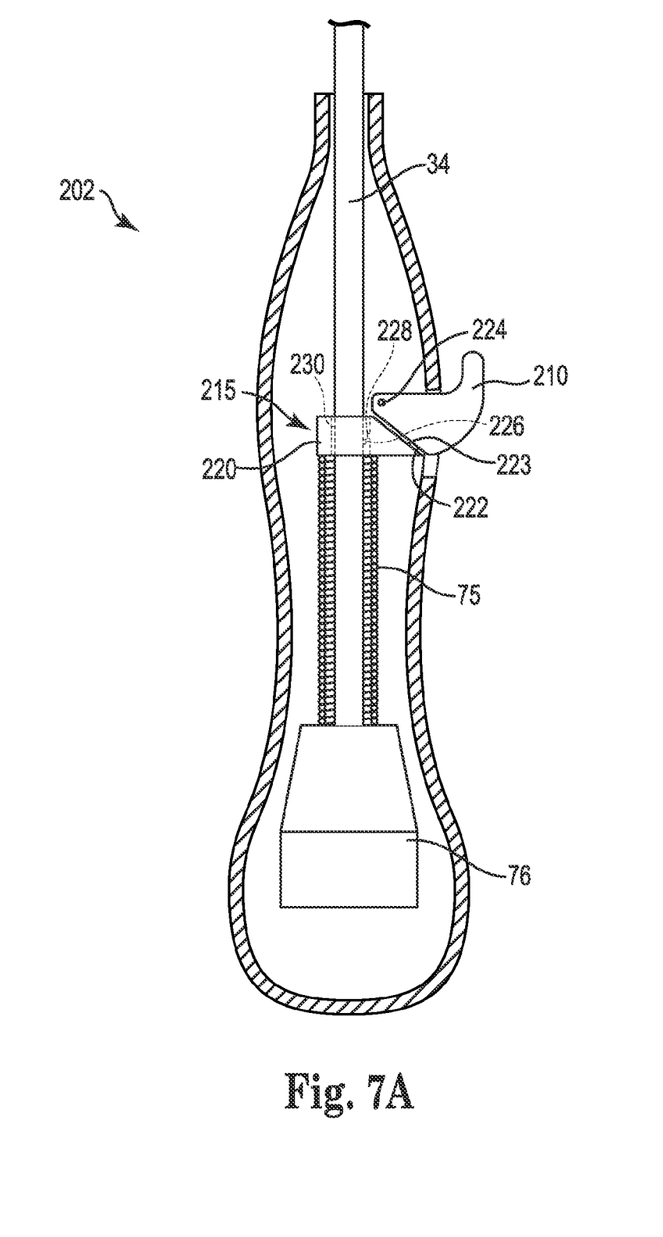

FIG. 7A is a top cross-sectional view of the handle 202 with the release lever 210 in a neutral position. The spring 75 is captured between the spring pusher 76 and a plate 220 attached to the rod 34. One embodiment of the handle 202 provides a release mechanism 215 that employs cooperating cam surfaces 222, 223 that operate to move the rod 34 rearward (or a distance in a proximal direction) to separate the suture capsule 46 from the needle 32 as analogously illustrated in FIG. 5D above.

In particular, the release mechanism 215 is configured to allow the rod 34 to freely move longitudinally through the plate 220 in the distal direction. The release mechanism 215 includes a shoulder 226 attached to the rod 34 and a flange 228 attached to the plate 220. The shoulder 226 is provided with clearance to allow the rod to freely move in the distal direction through channel 230. The shoulder 226 is configured to engage with a flange 228 of the plate 220 when the cam surface 222 of the release lever 210 presses against the cam surface 223 of the plate 220 and moves the plate 220 laterally (as illustrated at 242 in FIG. 7B). Movement of the plate 220 by action of the release lever 210 shifts the plate 220 laterally to allow the flange 228 to engage with the shoulder 226, thus moving the rod 34 rearward in the proximal direction in response to the contact at the cam surfaces 222, 223. Thus, in the neutral position illustrated in FIG. 7A, the rod 34 is free to move through the plate 220 longitudinally in the forward or distal direction in response to the movement of the actuator 30 (FIG. 6).

Figure 7B:
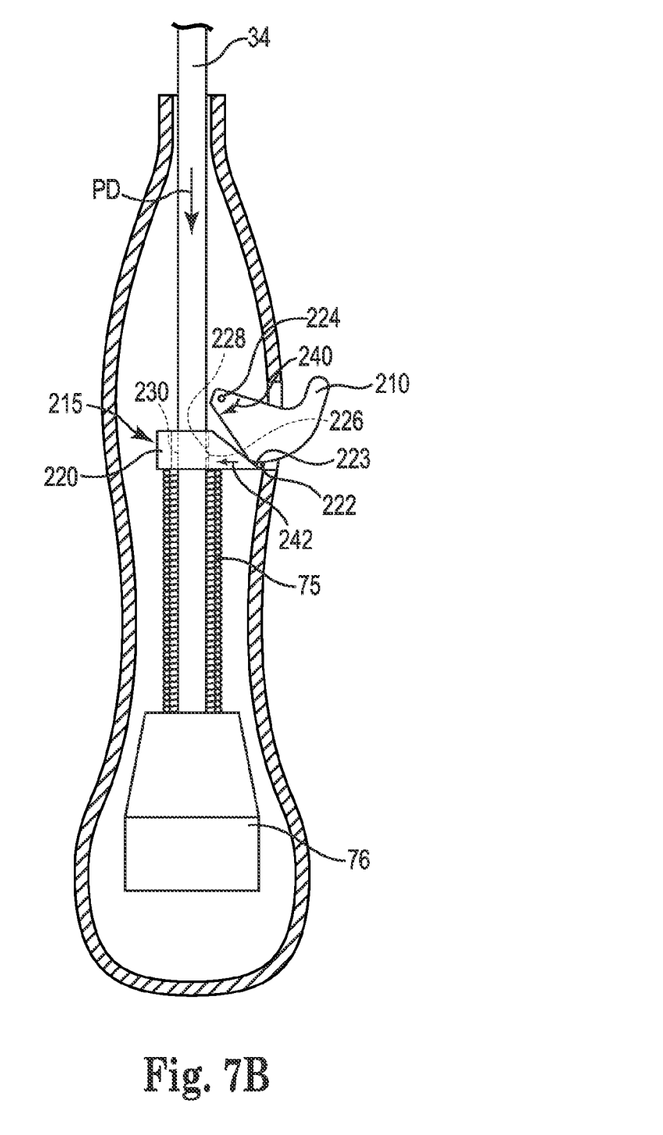

FIG. 7B is a top cross-sectional view of the handle 202 with the release lever 210 activated to move the rod 34 an additional distance in the proximal direction to separate the suture capsule 46 from the needle 32. The release lever 210 is configured to be activated with a finger, for example the index finger, of the surgeon's hand that is controlling the handle 202. Pulling the release lever 210 rearward in the proximal direction rotates the lever 210 at 240 and engages the cam surface 222 of the trigger 210 with the cam surface 223 of the plate 220. The release lever 210 moves the plate 220 laterally at 242 to allow the flange 228 of the plate 220 to engage with the shoulder 226 of the rod 34. In this manner, the plate 220 is engaged with the rod 34 by interaction between the shoulder 226 and the flange 228. The movement of the release lever 210 about the pivot point 224 thus operates to move the rod 34 an additional distance in the proximal direction PD (or release direction PD), which shears the suture capsule 46 against the guide pin 130 as illustrated in FIG. 5D. The spring 75 is compressed when the trigger 210 is squeezed. The spring 75 returns the trigger 210 to its rest position when the trigger 210 is released.

In a separate embodiment, the plate 220 is optional and the release lever 210 is rigidly attached to the rod 34 and a rearward movement of the release lever 210 directly moves the rod 34 rearward in the proximal direction to separate the suture capsule 46 from the needle 32 as analogously illustrated in FIG. 5D.

Figure 8:
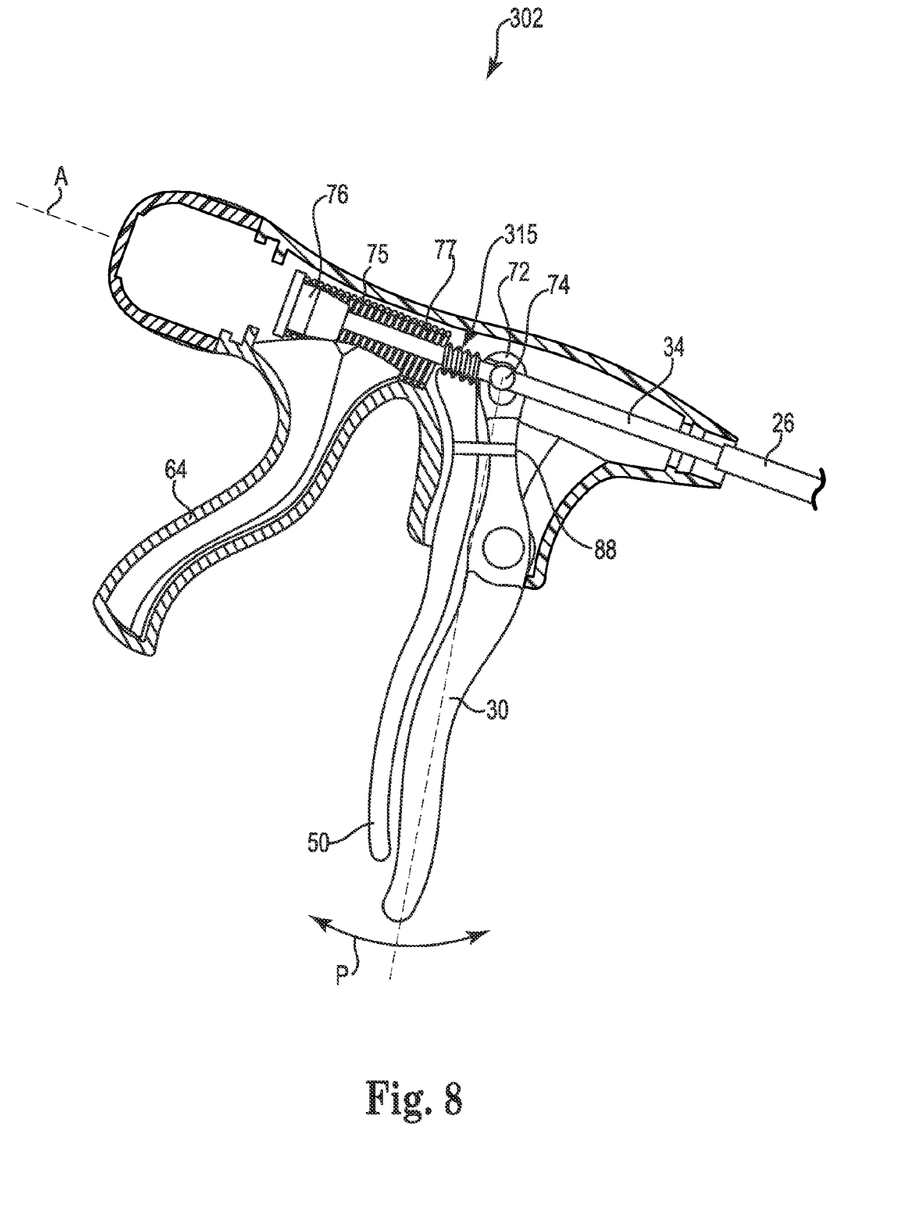
FIG. 8 is a side cross-sectional view of one embodiment of a tissue suturing device including.

FIG. 8 is a side cross-sectional view of one embodiment of a handle 302 suitable for use with the device 20 described above. The handle 302 includes the actuator 30 that is configured to move longitudinally in the plain P parallel with the longitudinal axis A to drive the rod 34 in the distal direction and to retract the rod 34 in the proximal direction to place the sure 48 into tissue. The release lever 50' is provided to move the rod 34 an additional distance in the proximal direction to disengage the suture capsule 46 from the needle 32 (as illustrated in FIG. 5D). In one embodiment, the handle 302 includes a release mechanism 315 that provides the rod 34 with a first gear surface 320 that meshes with a second gear surface 322 provided on an end of the release lever 50'. In one embodiment, the gear surfaces 320, 322 are provided as a worm gear that translates the lateral motion of release lever 50 into a longitudinal motion of the rod 34.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A tissue suturing device comprising:
   a handle including an actuator coupled to a distal half of the handle;
   a head defining a head perimeter and including a needle port and a capsule cavity located within the head perimeter, the needle port storing a needle that is connected with the actuator by a rod and the capsule cavity sized to retain a suture capsule attached to a length of suture, the actuator provided with a slotted head and the rod including a pinion inserted into the slotted head; and
   a release mechanism connected with the rod and located on the distal half of the handle, the release mechanism including a cable, a pulley, and a release lever, with the cable connected to a proximal end of the rod and extending over both the pulley and the pinion and connected to the release lever;
      wherein the needle is movable within the head perimeter to engage with the suture capsule and place the suture capsule into the needle port, and the release mechanism is operable to move the rod a distance in a proximal direction to separate the suture capsule from the needle.

2. The tissue suturing device of claim 1, wherein the release mechanism is connected to the actuator and the actuator is configured to move within a plane that is parallel with a longitudinal axis of the rod.

3. The tissue suturing device of claim 2, wherein the release mechanism is configured to move with the actuator within the plane that is parallel with the longitudinal axis of the rod and the release mechanism is additionally configured to move substantially perpendicular with the plane that is parallel with the longitudinal axis of the rod.

4. The tissue suturing device of claim 1, wherein the handle includes a thumb brace located on a proximal half of the handle.

5. The tissue suturing device of claim 1, wherein the release mechanism is operable to move the rod by a distance of between 0.5-2 mm in the proximal direction to separate the suture capsule from the needle.

6. The tissue suturing device of claim 1, wherein the actuator and the release lever are configured for operation with only one hand.

7. The tissue suturing device of claim 1, wherein the proximal portion of the head provides a needle exit port and the release lever is operable to move the rod in the proximal direction to shear the capsule against a wall of the needle exit port to separate the capsule from the needle.

8. The tissue suturing device of claim 1, wherein the handle has a top surface and a bottom surface, and the actuator is coupled with the rod and extends through the bottom surface of the handle, and the release lever is coupled with the rod and extends through the bottom surface of the handle proximal relative to the actuator.

9. The tissue suturing device of claim 1, wherein the actuator and the release lever are both operable to move the needle.

* * * * *